(12) United States Patent
Wardlaw

(10) Patent No.: US 7,628,532 B2
(45) Date of Patent: Dec. 8, 2009

(54) APPARATUS AND METHOD INCORPORATING AN INDICATOR CHAMBER FOR ELEVATED TEMPERATURE PRESSURE VESSEL OR WELD TESTING

(76) Inventor: Louis J. Wardlaw, c/o Hot-Hed Inc., 5322 Addicks-Satsuma Rd., Houston, TX (US) 77284

(*) Notice: Subject to any disclaimer, the term of this patent is extended or adjusted under 35 U.S.C. 154(b) by 125 days.

(21) Appl. No.: 11/788,874

(22) Filed: Apr. 19, 2007

(65) Prior Publication Data
US 2008/0259991 A1    Oct. 23, 2008

(51) Int. Cl.
*G01M 3/22* (2006.01)
*G01N 25/72* (2006.01)

(52) U.S. Cl. ............................ 374/4; 73/40.7
(58) Field of Classification Search ............ 73/40.7, 73/46; 374/4, 5
See application file for complete search history.

(56) References Cited

U.S. PATENT DOCUMENTS 3,082,760 A * 3/1963 Jaeger ................ 126/271.2 R
4,507,082 A * 3/1985 Wardlaw, III ............... 432/224
4,596,135 A * 6/1986 Wardlaw, III ................ 73/40.7
2006/0000261 A1* 1/2006 Wardlaw, III ................ 73/40.7

* cited by examiner

*Primary Examiner*—Andre J Allen

(57) ABSTRACT

In a method and system for testing the integrity of pressure vessels, or welds on flanges or the like, at elevated temperatures, a pressurized mixture of a gaseous environmentally safe composition is formed within an indicator chamber in a housing receiving a pressurized gas and containing a surface in the chamber upon which is placed an indicator composition including a marker component, whereby the marker component is carried by the carrier gas from within the chamber and through a conduit to the pressure vessel or weld area. The carrier gas and the indicator or marker component are injected in an area between the inner and outer weld of a terminal flange welded to a tubular pipe section or casing. The pressurized composition includes a marker component or sub-composition which is detected by a detection apparatus which scans the pressure vessel area to be tested, or weld area. The pressure of the gas may also be monitored to observe losses in pressure indicative of flaws in the pressure vessel area or welds. The integrity of the pressure vessel or welds is tested at elevated temperature permitting remedial repairs to be made without reheating the work area of the pressure vessel or on a tubular pipe or casing.

17 Claims, 1 Drawing Sheet

APPARATUS AND METHOD INCORPORATING AN INDICATOR CHAMBER FOR ELEVATED TEMPERATURE PRESSURE VESSEL OR WELD TESTING

BACKGROUND OF THE DISCLOSURE (1) Field of the Invention

This invention is directed to a method for testing the integrity of welds, or welded or other connections in a pressure vessel, and particularly, a process for pressure testing the integrity of such connections or welds at elevated temperatures using a pressurized gas composition formed within an indicator chamber wherein an inert gas is introduced to come into contact with and carry a marker component of an indicator composition, to locate flaws which may be present in the pressure vessel or welds.

(2) Brief Description of the Prior Art

In drilling an oil well, it is often necessary to install wellheads of various sizes of large diameter pipe. Several sizes of pipe or casing may be installed in a well. The well might include, as an example, a 36 inch driver pipe. There may also be a 20 inch casing, 13 and ⅜ inch casing and 9 and ⅝ inch casing. It is necessary to install a terminate flange or wellhead at every change of size. The wellhead is typically installed by first cutting the casing, preheating the casing, then welding the wellhead in place. The wellhead is necessary to mount other equipment or to otherwise install the next casing string. Often, this procedure requires cutting a very thick wall casing, even in the range of 1½ inch thick and thereafter making a multi-pass welded bead to attach the wellhead. To obtain a quality weld, the temperature of the pipe in the area of the weld must be raised to the welding temperature of the pipe or casing prior to actual welding. A typical welding temperature for pipe or casing material is in the range of 500.degree. F. Consequently, a tremendous amount of preheating is required to obtain a quality weld.

Preheating is often a problem, particularly for drilling rigs located at sea. In inclement weather, wind shields must be installed and a number of welders will position their torches on the casing and wellhead to preheated for perhaps 4 to 6 inches below the casing head in length to perhaps 500.degree. F. This is difficult and time consuming.

Certain devices have been provided heretofore to serve as pre-heaters. In U.S. Pat. No. 4,507,082 to Wardlaw, the inventor of the present disclosure, a preheating apparatus is described which heats the casing and wellhead from the interior. Other pre-heater devices are also available as typified by the patent of Jaeger, U.S. Pat. No. 3,082,760.

While a number of apparatus have been developed for preheating the casing and wellhead to welding temperatures, relatively little has been done in the area of testing or proving the integrity of the welds. The integrity of the welds connecting the wellhead or terminal flange to the casing, however, is critical to the safe completion of a well. When drilling an oil well, tremendous pressures may be encountered requiring that all connections or welds be leak-proof. This is particularly true for connection of the wellhead which includes other apparatus mounted thereon.

It has long been recognized that proving the integrity of welds, or connection points when assembling two or more units together to form a "pressure vessel" is desirable and necessary. To this end, terminal flanges or wellheads are provided with an internal circumferential groove, which groove is located between the inner and outer weld upon welding the wellhead to the casing. A port provides access to the groove. Thus, the conventional method for testing the integrity of welds includes the connection of a pressure pump to the port and pumping fluid into the groove and observing any pressure losses. Fluids such as oil, water, or antifreeze are typically used. Prior to injection of the fluid, however, the casing must be permitted to cool to approximately 200.degree. F. or less to avoid thermal shock at the weld. Rapid cooling can damage the metallurgy of the casing and wellhead material. The customary method of proving the integrity of welds is to permit the wellhead casing to gradually cool to a temperature of 200.degree. F. or less prior to injection of a fluid into the test groove to verify that no flaws or cracks are present in the welds. This procedure is very time consuming and in the event that flaws in the weld are located, the wellhead and casing must be reheated to the welding temperature to repair the flaws or cracks located in the initial welds. In addition, the test groove must be cleaned of injection fluid prior to reheating.

U.S. Pat. No. 4,596,135, issued to the present applicant, discloses a testing procedure and system which uses a marker gas of conventional nature, such as Freon. However, in recent years, Freon and other chlorine-containing halogenic gaseous substances have been prohibited as refrigerants and other commercialized uses by many nations in the world because of the belief that it destroys the protective ozone belt in the atmosphere. Other nations have, however, either not barred use of such gases or have not restricted their use to such a point that they cannot be used in very limited amounts for some uses.

Several other gas compositions have been suggested for many commercial applications, but their overall use and acceptance has been slow due to several disadvantages, not the least of which is the corrosive side effect that some of the newer gas compositions may have when exposed to some exotic metals sometimes found in industrialized applications.

In addition to problems associated with the use of chlorine-containing halogenic gases, any type of marker composition that is desired to be carried with an inert gas, such as nitrogen, has, prior hereto, been required to be provided in bottles or similar transportable containers which, in cases in which the weld to be tested is on an offshore well head, must be transported by boat to the particular work location. The transport of such bottles is costly, time consuming, and their stacking and storage on the platform or similar work location takes up valuable space.

The process and system of the present disclosure overcomes the disadvantages of prior art weld verification techniques, particularly where gases which have been proven to be environmentally dangerous have been utilized. It uses an inert gas, such as nitrogen, which is readily available in storage containers on the platform or other operations location, and which is used for may other applications. The need for bottled indicator compositions is eliminated by the use of a housing including a locator chamber wherein the inert gas is introduced into the chamber and caused to pass over or through or across means for receipt of an indicator composition, such as a removable or other surface means, such as a cloth, sponge, cotton balls, or the like, upon which the indicator composition has been previously impregnated.

The process of the present disclosure may be carried out at elevated temperatures thereby eliminating the time consuming cool down period prior to testing and the reheating period in the event remedial repairs to the welds required and by preferably incorporating a nonchloride-, nonchlorine-containing constituent as a marker. Conventional marker components containing a chlorine component or a mercaptan may also be used where permitted by law. Hydrocarbons, such as dielse and gasoline may also be used.

SUMMARY OF THE INVENTION

The present disclosure is directed to a system and process for verifying the integrity of welds or other connection points in the assembly or testing of pressure vessels, at elevated temperatures. When used herein, and, particularly, in the appended claims, "weld" or "welds" is intended to include connection points or means for two or more conduits, pipes, or components of a flange or pressure vessel. The system comprises a source of pressurized gas. An indicator chamber in a housing is provided, the housing having upstream and downstream ends. Means are defined within the chamber housing between the housing ends for receipt of an indicator composition impregnated onto a surface within the chamber. A first conduit is connected between the source of the pressurized gas and the upstream end of the housing for introducing the gas through the conduit and into the chamber and across the removable surface, to thereafter carry the marker component in the indicator composition in the carrier gas and out of the chamber. A second conduit is secured between the downstream end of the chamber housing and an injection port in the wellhead, for transmitting the combined carrier gas and the marker component in the indicator composition therein and over (or across) the weld. A gas detector probe is also provided for detecting any indicator or marker component leaking through the weld, when fluid communication is established between the pressurized gas composition and the weld while the weld is maintained at an elevated welding temperature for detecting flaws in the weld at the elevated temperature. Leaks or other flaws in the welds may also be observed by monitoring a pressure gauge on the inert gas container or the housing for the chamber for any loss of pressure which would indicate the presence of a leak.

DETAILED DESCRIPTION OF THE PREFERRED EMBODIMENT

Figure 1:
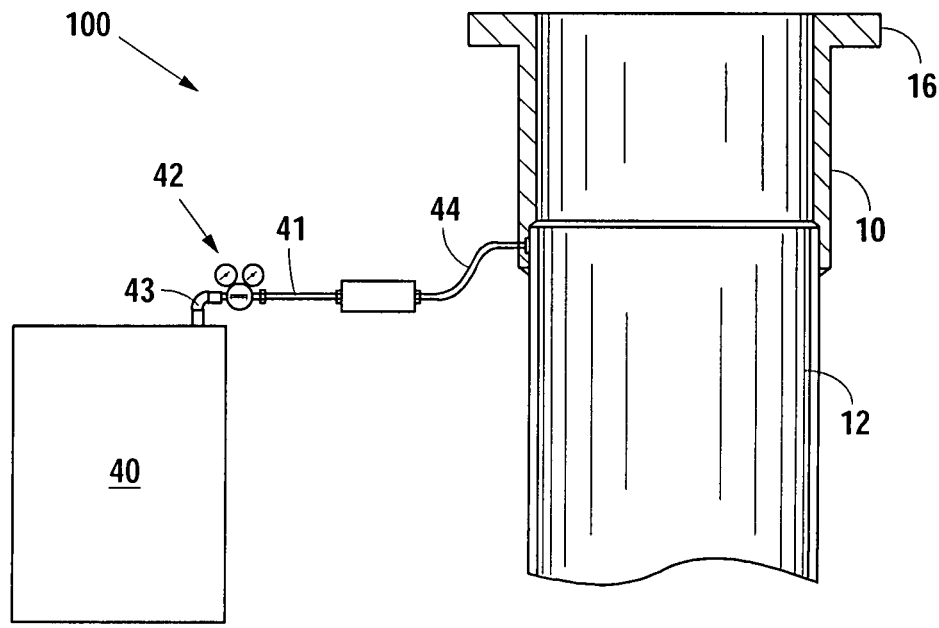
FIG. 1 is a cross-sectional view illustrating the system of the present disclosure connected to test the integrity of the welds connecting a wellhead to a casing.

Attention is first directed to FIG. 1 of the drawings, which shows the general configuration of the system 100 for verifying the integrity of the welds connecting a wellhead or terminal flange 10 to a casing 12.

Assume, for purposes of illustration, that the casing 12 is a large diameter casing having a wall thickness conforming with industry standards. The casing 12 can range from ½ inch thick to about 1½ inch or greater. The wellhead 10 is connected to the casing 12. The wellhead 10 is constructed with an internal shoulder 14 (FIG. 2) to abut the end of the casing 12.

The wellhead 10 is generally cylindrical and open at each end. A peripheral, outwardly extending flange 16 is provided about the upper end of the wellhead 10 for connection to other equipment.

Figure 2:
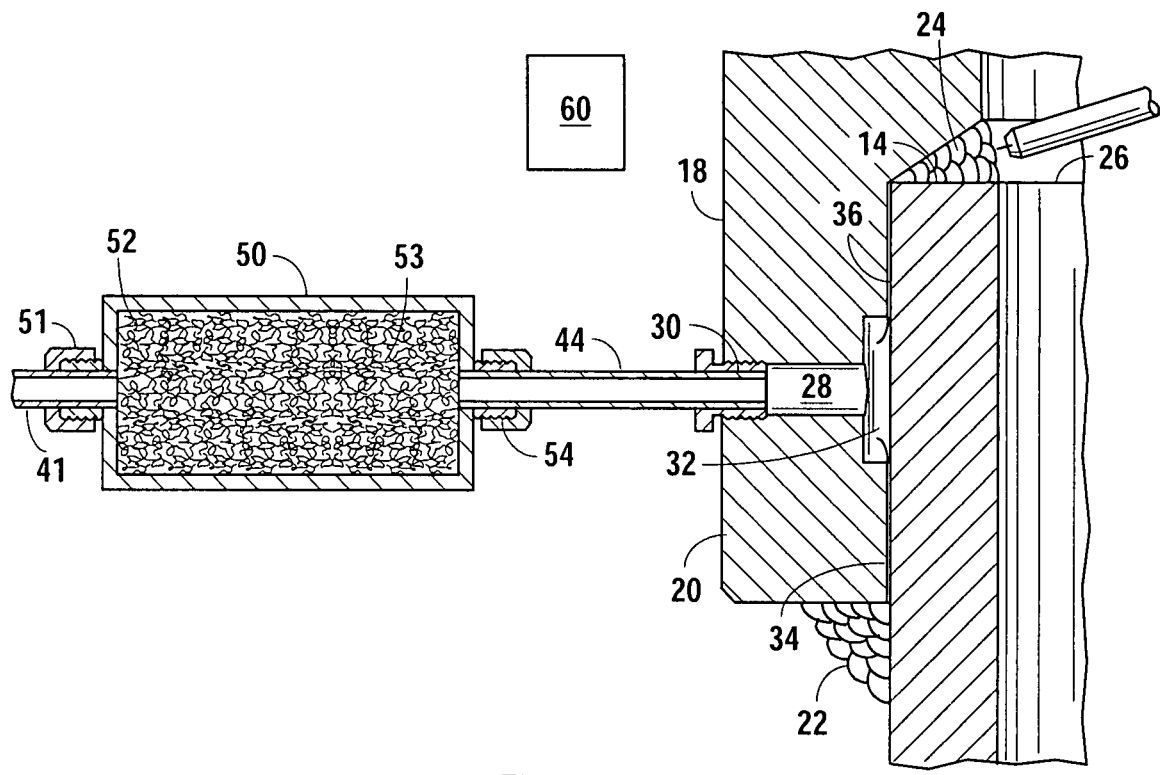
FIG. 2 is an enlarged cross-sectional view of the system including the indicator chamber housing and the removable surface therein, and further illustrating the welds and injection port and the fluid communication established between the injection port and the welds.

As shown in FIG. 2, at the opposite end of the wellhead 10, a cylindrical portion 18 extends from the shoulder 14 which telescopes over the end of the casing 12. The end or edge of the cylindrical portion 18 is defined by a flat circumferential surface 20. A multi-pass bead 22 is formed joining the surface 20 and the external surface of the casing 12.

A finish bead 24 is formed joining the end 26 of the casing 12 to the shoulder 14 of the wellhead 10.

The bead 22 is formed first to fully and completely anchor the wellhead 10 to the casing 12. The weld 22 is a high quality weld, subject to 100% inspection, and must usually be formed in many passes.

Prior to welding, it is very important to preheat the casing 12 to a specified temperature, typically in the range of 500.degree. F. Failure to evenly preheat the casing 12 may damage the welds 22 and 24. Likewise, rapid cooling after the welds 22 and 24 have been formed may crack or fracture the welds 22 and 24.

As previously mentioned, it is a well-known practice to test the integrity of the welds 22 and 24. To this end, the cylindrical portion 18 is provided with an injection port 28. The injection port 28 is internally threaded at 30 and opens into a circumferential groove 32 formed on the internal cylindrical surface of the cylindrical portion 18. When the cylindrical portion 18 is telescoped over the end of the casing 12 as shown in FIG. 2, the groove 32 and casing 12 form a fluid chamber or gap therebetween.

The wellhead 10 and casing 12 are sized so that when telescoped together, a metal-to-metal contact is established between the internal surface of the cylindrical portion 18 and the external surface of the casing 12. For illustrative purposes, however, gaps 34 and 36 are shown in FIG. 2 to illustrate that fluid communication is established between the welds 22, 24 and the fluid chamber or groove 32.

Referring again to FIG. 1, the pressurized container 40 of the system of the present disclosure contains nitrogen or other inert gas and is readily available. Immediately above the container 40 is a first conduit or line 41 upon which is connected conventional gauges 42 for measuring the pressure in the container 40 the conduit or line 41 is connected to an upstream opening or end 51 of an indicator chamber housing 50 having therein a chamber 52. A series of cotton balls, cloth, or other similar surface means 53 is disposed throughout the chamber 52. Before being placed within the housing chamber 52, the surface means 53 has been saturated in a pre-prepared indicator composition, described in further detail, below. The housing 50 may be provided in two or more sealable parts, for easy placement and removal of the surface means 53.

The container 40 is a fairly large volume high pressure gas container provided with a valve 43. An upstream valve conduit carries the gauges 42 and the valve 43 and extends to the opening 51 of the housing 50 for fluid communication with the chamber 52. A similar, second or downstream conduit member 44 extends for a downstream end 54 on the housing 50 at one end, and extends to and is secured into the cylindrical portion 18 and through the threaded opening or port 30.

Interior of the housing chamber 52 is placed one or more cloths or other solids, balls, or other materials 53 upon which has been saturated a gas composition, as described below. As the inert gas, such as nitrogen is transmitted from the container 40, through the opened valve 43 and into the conduit member 41, the inert gas will pass over and be injected across the material or solid 53 containing the gas composition, and will act as the carrier gas for the composition, which passes out of the downstream end 54 of the chamber 53, through the conduit member 44, thence into the space 32 between the welds 22 and 24.

The gas composition transmitted the downstream end 54 of the chamber 52 provides sufficient pressure within industry standards, typically in the range of 150-1500 psi to test for any flaws or cracks which may be present in the weld beads 22 and 24. This gas indicator composition also include a marker which may be easily detected as it leaks through the welds 22 and 24. By way of example and for illustrative purposes only, compressed nitrogen may be used to supply the pressure necessary for testing the integrity of the welds 22 and 24.

In recent years, there has been considerable attention directed to the use of certain chlorofluorocarbons (CFC's) and hydrochlorofluorocarbons (HCFC's) because they are believed to attack and deplete the earth's ozone layer. Accordingly, the present invention contemplates the use of a marker that does not contain the undesired chlorinated components that are harmful to the ozone belt. The invention contemplated the use as a marker, and in combination with the other components herein, a non-chlorine-containing marker composition, such as a single fluorinated hydrocarbon or an azeotropic or azeotrobe-like composition that includes one or more fluorinated hydrocarbons. The present invention preferably relates to the use of non-chlorine-containing marker probe components such as compositions of hexafluoropropane and a hydrocarbon having from 1 to 5 carbon atoms or dimethyl ether. Examples of hydrocarbons having from 1 to 5 carbon atoms include butane, cyclopropane, isobutane, propane. Examples of the inventive compositions include compositions of 1,1,2,2,3,3-hexafluoropropane (HFC-236ca) and butane, cyclopropane, isobutane or propane; 1,1,1,2,2,3-hexafluoropropane (HFC-236cb) and butane, cyclopropane, dimethyl ether (DME), isobutane or propane; 1,1,2,3,3,3-hexafluoropropane (HFC-236ea) and butane, cyclopropane, DME, isobutane or propane; and 1,1,1,3,3,3-hexafluoropropane (HFC-236fa) and DME, butane, cyclopropane, isobutane or propane. Further, the invention relates to the discovery of binary azeotropic or azeotrope-like compositions comprising effective amounts of 1,1,2,2,3,3-hexafluoropropane and butane, cyclopropane, isobutane or propane; 1,1,1,2,2,3-hexafluoropropane and butane, cyclopropane, DME, isobutane or propane; 1,1,2,3,3,3-hexafluoropropane and butane, cyclopropane, DME, isobutane or propane; and 1,1,1,3,3,3-hexafluoropropane and DME, butane, cyclopropane, isobutane or propane to form an azeotropic or azeotrope-like composition.

The term "azeotropic compositions" in connection with this invention includes both the azeotrope and compositions that behave essentially like an azeotrope in that they boil at substantially the same temperature as the corresponding azeotrope. Preferably, the boiling point of an azeotropic composition at ambient pressure is within about 1.degree. C. of the boiling point of its azeotrope measured at the same pressure. More preferably, the azeotropic compositions will boil at temperatures that are within about 0.5.degree. C. of the boiling points of their corresponding azeotropes. It will be understood that the concentrations of the hydrofluorocarbon ether and organic solvent in a particular azeotropic composition may vary substantially from the amounts contained in the composition's corresponding azeotrope, and the magnitude of such permissible variation depends upon the organic solvent used to make the composition. Preferably, the concentrations of hydrofluorocarbon ether and organic solvent in an azeotropic composition vary no more than about ten percent from the concentrations of such components contained in the azeotrope formed between them at ambient pressure. More preferably, the concentrations are within about five percent of those contained in the azeotrope. Most preferably, the azeotropic composition contains essentially the same concentrations of the ether and solvent as are contained in the azeotrope formed between them at ambient pressure. Where the concentrations of ether and organic solvent in an azeotropic composition differ from the concentrations contained in the corresponding azeotrope, the preferred compositions contain a concentration of the ether that is in excess of the ether's concentration in the azeotrope. Such compositions are likely to be less flammable than azeotropic compositions in which the organic solvent is present in a concentration that is in excess of its concentration in the azeotrope.

The preferred azeotropic composition of the present invention can be used as a replacement for CFCs and HCFCs in a variety of applications in which CFCs and HCFCs have traditionally been employed. In particular, azeotropic compositions in accordance with the present invention are suitable candidates for the replacement of CFC-11 and/or CFC-113. In particular, the azeotropic compositions may be used in cleaning, in heat transfer processes, as refrigerants, as a reaction medium, as a blowing agent, as a coating liquid, and the like.

The preferred azeotropic compositions according to this invention are mixtures of hydrofluorocarbon ether and second and optionally third component which, if fractionally distilled, produce a distillate fraction that is an azeotrope of the hydrofluorocarbon ether and the second and optionally third component. The azeotropic compositions boil at temperatures that are essentially the same as the boiling points of their corresponding azeotropes. Preferably, the boiling point of an azeotropic composition at ambient pressure is within about 1.degree. C. of the boiling point of its corresponding azeotrope measured at the same pressure. More preferably, the azeotropic compositions will boil at temperatures that are within about 0.5.degree. C. of the boiling points of their corresponding azeotropes. The concentrations of the hydrofluorocarbon ether and second and optionally third component in a particular azeotropic composition may vary substantially from the amounts contained in the composition's corresponding azeotrope, and the magnitude of such permissible variation depends upon the second and optionally third component used to make the azeotropic composition. Preferably, the concentrations of hydrofluorocarbon ether and second and optionally third component in an azeotropic composition vary no more than about ten percent from the concentrations of such components contained in the azeotrope formed between them at ambient pressure. More preferably, the concentrations are within about five percent of those contained in the azeotrope. Most preferably, the azeotropic composition contains essentially the same concentrations of the ether and second and optionally third component as are contained in the azeotrope formed between them at ambient pressure. Where the concentrations of ether and second and optionally third component in an azeotropic composition differ from the concentrations contained in the corresponding azeotrope, the preferred compositions contain a concentration of the ether that is in excess of the ether's concentration in the azeotrope. Such compositions are likely to be less flammable than azeotropic compositions in which the second and optionally third component is present in a concentration that is in excess of its concentration in the azeotrope. The most preferred azeotropic compositions will exhibit no significant change in the solvent power of the compositions over time.

The language "consisting of" used in describing the preferred azeotropic or other compositions of the invention is not intended to exclude the presence of minor amounts of other materials which do not significantly alter the azeotropic behavior of the composition. Accordingly, the preferred azeotropic compositions of this invention may also contain, in addition to the hydrofluorocarbon ether and second and optionally third component, small amounts of other compounds which do not interfere in the formation of the azeotrope. For example, small amounts of surfactants may be present in the azeotropic compositions of the invention to improve the dispersibility or solubility of materials, such as water or coating materials (e.g., perfluoropolyether lubricants and fluoropolymers), in the azeotropic composition.

The characteristics of azeotropes are discussed in detail in Merchant, U.S. Pat. No. 5,064,560 (see, in particular, col. 4, lines 7-48).

The hydrofluorocarbon ether preferably used in the present invention is $C_3F_7$—$OCH_3$ and includes the pure isomers n-$C_3F_7$—$OCH_3$ and $CF_3$—$CF(OCH_3)$--$CF_3$ (=i—$C_3F_7$ $F_7$—$OCH_3$) as well as mixtures of these isomers. Most preferred in the present invention is pure n-$C_3F_7$—$OCH_3$.

The hydrofluorocarbon ether can be prepared by alkylation of perfluorinated alkoxides prepared by the reaction of the corresponding perfluorinated acyl fluoride or perfluorinated ketone with any suitable source of anhydrous fluoride ion such as anhydrous alkali metal fluoride (e.g., potassium fluoride or cesium fluoride) or anhydrous silver fluoride in an anhydrous polar, aprotic solvent in the presence of a quaternary ammonium compound such as "ADOGEN 464" available from the Aldrich Chemical Company. General preparative methods for the ethers are also described in French Patent No. 2,287,432, German Patent No. 1,294,949, and in Assignee's co-pending application titled "Process for Production of Hydrofluoroethers," U.S. Ser. No. 08/632,697.

Suitable alkylating agents for use in the preparation include dimethyl sulfate, methyl iodide, methyl p-toluenesulfonate, methyl perfluoromethanesulfonate and the like. Suitable polar, aprotic solvents include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

Perfluorinated acyl fluorides (for use in preparing the hydrofluorocarbon ether) can be prepared by electrochemical fluorination (ECF) of the corresponding hydrocarbon carboxylic acid (or a derivative thereof), using either anhydrous hydrogen fluoride (Simons ECF) or KF.2HF (Phillips ECF) as the electrolyte. Perfluorinated acyl fluorides and perfluorinated ketones can also be prepared by dissociation of perfluorinated carboxylic acid esters (which can be prepared from the corresponding hydrocarbon or partially-fluorinated carboxylic acid esters by direct fluorination with fluorine gas). Dissociation can be achieved by contacting the perfluorinated ester with a source of fluoride ion under reacting conditions (see the methods described in U.S. Pat. No. 3,900,372 (Childs) and U.S. Pat. No. 5,466,877 (Moore), the description of which is incorporated herein by reference) or by combining the ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents.

Initiating reagents which can be employed in the dissociation are those gaseous or liquid, non-hydroxylic nucleophiles and mixtures of gaseous, liquid, or solid, non-hydroxylic nucleophile(s) and solvent (hereinafter termed "solvent mixtures") which are capable of nucleophilic reaction with perfluorinated esters. The presence of small amounts of hydroxylic nucleophiles can be tolerated. Suitable gaseous or liquid, non-hydroxylic nucleophiles include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, e.g., fluoride, cyanide, cyanate, iodide, chloride, bromide, acetate, mercaptide, alkoxide, thiocyanate, azide, trimethylsilyl difluoride, bisulfite, and bifluoride anions, which can be utilized in the form of alkali metal, ammonium, alkyl-substituted ammonium (mono-, di-, tri-, or tetra-substituted), or quaternary phosphonium salts, and mixtures thereof. Such salts are in general commercially available but, if desired, can be prepared by known methods, e.g., those described by M. C. Sneed and R. C. Brasted in Comprehensive Inorganic Chemistry, Volume Six (The Alkali Metals), pages 61-64, D. Van Nostrand Company, Inc., New York (1957), and by H. Kobler et al. in Justus Liebigs Ann. Chem., 1978, 1937. 1,4-diazabicyclo[2.2.2]octane and the like are also suitable solid nucleophiles.

The hydrofluorocarbon ethers preferably used to prepare the azeotropic compositions of this invention do not deplete the ozone in the earth's atmosphere and have surprisingly short atmospheric lifetimes thereby minimizing their impact on global warming. An atmospheric lifetime for the hydrofluorocarbon ether was reported by S. Misaki and A. Sekiya at the International Conference On Ozone Protection Technologies, Conference Proceedings, Oct. 21-23, 1996, Washington, D.C. Many hydrofluorocarbon ether has a relatively short estimated atmospheric lifetime and relatively small global warming potential. These hydrofluorocarbon ethers also have a significantly shorter estimated atmospheric lifetime than the corresponding hydrofluorocarbon alkanes.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, that is, the admixture distills/refluxes without substantial composition change. Another way to characterize an azeotrope-like composition is that the bubble point vapor pressure and the dew point vapor pressure of the composition at a particular temperature are substantially the same.

It is recognized in the art that a composition is azeotrope-like if, after 50 weight percent of the composition is removed such as by evaporation or boiling off, the difference in vapor pressure between the original composition and the composition remaining after 50 weight percent of the original composition has been removed is less than 10 percent, when measured in absolute units. By absolute units, it is meant measurements of pressure and, for example, psia, atmospheres, bars, torr, dynes per square centimeter, millimeters of mercury, inches of water and other equivalent terms well known in the art. If an azeotrope is present, there is no difference in vapor pressure between the original composition and the composition remaining after 50 weight percent of the original composition has been removed.

Therefore, preferably included in this invention are non-chlorine-containing marker composition probes of effective amounts of 1,1,2,2,3,3-hexafluoropropane and butane, cyclopropane, isobutane or propane; 1,1,1,2,2,3-hexafluoropropane and butane, cyclopropane, DME, isobutane or propane; 1,1,2,3,3,3-hexafluoropropane and butane, DME, cyclopropane, isobutane or propane; and 1,1,1,3,3,3-hexafluoropropane and DME, butane, cyclopropane, isobutane or propane such that after 50 weight percent of an original composition is evaporated or boiled off to produce a remaining composition, the difference in the vapor pressure between the original composition and the remaining composition is 10 percent or less.

For compositions that are azeotropic, there is usually some range of compositions around the azeotrope that, for a maximum boiling azeotrope, have boiling points at a particular pressure higher than the pure components of the composition at that pressure and have vapor pressures lower at a particular temperature than the pure components of the composition at that temperature, and that, for a minimum boiling azeotrope, have boiling points at a particular pressure lower than the pure components of the composition at that pressure and have vapor pressures higher at a particular temperature than the pure components of the composition at that temperature. Boiling temperatures and vapor pressures above or below that of the pure components are caused by unexpected intermolecular forces between and among the molecules of the compositions, which can be a combination of repulsive and attractive forces such as van der Waals forces and hydrogen bonding.

The range of compositions that have a maximum or minimum boiling point at a particular pressure, or a maximum or minimum vapor pressure at a particular temperature, may or may not be coextensive with the range of compositions that are substantially constant boiling. In those cases where the range of compositions that have maximum or minimum boiling temperatures at a particular pressure, or maximum or minimum vapor pressures at a particular temperature, are broader than the range of compositions that are substantially constant boiling according to the change in vapor pressure of the composition when 50 weight percent is evaporated, the unexpected intermolecular forces are nonetheless believed important in that the refrigerant compositions having those forces that are not substantially constant boiling may exhibit unexpected increases in the capacity or efficiency versus the components of the refrigerant composition.

The marker or indicator composition used and described herein and immediately above is easily detectable at very low concentrations, may be utilized in the pressurized gas mixture of the system of the present disclosure. It is understood, however, that other indicator compositions within the scope of the claims herein may also be used to form the indicator composition. The system of the present invention requires only that the inert gas carrier provide sufficient pressure and that the marker or indicator composition be detectable at relatively small concentrations.

Other FREON R12 non-chloine-containing replacements are contemplated for use in the present invention. Many of these replacements are useful as refrigerants. For example, DURACOOL 12a, commercially available from Duracool Limited, Edmonton, Alberta, Canada may be used in the marker composition and in the present invention. Another acceptable component in the marker composition is a refrigerant commonly referred to as R134. Still other useful components for the marking composition include HC-12a and OZ-12 (each being a registered trademark of OZ Technology, Inc., which has been generically identified by the Environmental Protection Agency as "Hydrocarbon Blend B".

To illustrate the benefits of the system described herein, it will be recalled that the pressurized container 40 is connected to the housing 50 and the injection port 28 using conduit members 41 and 44 upon completion of the weld beads 22 and 24. The temperature of the wellhead 10 and casing 12 is substantially near the welding temperature, having cooled only slightly while the connection at 30 is made. The valve 43 is opened permitting the compressed carrier gas from the permanent storage unit or container 40 to be injected into the chamber 52, where the gas picks up the detector composition and carries it to the groove 32. The valve 43 is closed and the pressure gauges 42 are monitored and loss of pressure is noted indicating that a flaw is present in the welds 22 and 24. The pressure gauges 42 provide the first indication of a flaw in the weld beads.

Each of the weld beads 22 and 24, however, is also checked with a marker gas detecting apparatus. A probe connected to the marker gas composition detecting apparatus 100 is passed over the welds 22 and 24 for detecting the marker gas composition passing through the welds 22 and 24. The detecting apparatus is calibrated to register very small concentrations of the marker gas composition, even in the range of parts per billion. Thus, the system of the present disclosure provides an effective means for locating flaws in the weld beads 22 and 24 at an elevated temperature substantially near the welding temperature.

If a leak is detected, the location and extent of the flaw can be determined by passing the probe 60 over the welds 22, 24 and observing the concentration of the marker gas registered by the marker gas composition detecting apparatus. The flaw is then ground out and remedial work is done while the wellhead 10 and casing 12 are still at the welding temperature. If no leaks are detected, the welds 22 and 24 may be conveniently retested when the wellhead temperature drops to ambient levels insuring that no flaws have developed in the well beads 22 and 24 during the cooling process.

The weld testing system of the present invention is a unique tool designed to pressure test the inside and outside weld on a socket type slip-on wellhead. Using an inert gas as a pressure medium instead of typical hydraulic fluid, the system requires no "cool down" time after welding is completed. Immediately following completion of welding the test nipple is screwed into the test port of the wellhead. Utilizing a quick-disconnect on a flex-line, the inert carrier gas (with a small trace of marker or detector composition) is used to test the welds by slowly pressuring up the test area while observing a pressure gauge on the assembly. When the desired level of pressure is reached the gas is shut-in and left for the test period. Should a drop in pressure be evident, a small electronic indicator probe is passed over the welds. This indicator probe can detect leaks as small as ½ ounce per year.

As stated previously, a mercaptan may also be used as the indicator component. Mercaptans are a class of organic compounds containing the group —SH bonded to a carbon atom. The volatile low-molecular-weight mercaptans have disagreeable odors. Mercaptans are found in crude petroleum, and methyl mercaptan is produced as a decay product of animal and vegetable matter. They also are produced by certain plants and animals; e.g., allyl mercaptan is released when onions are cut, butanethiol (butyl mercaptan) derivatives are present in skunk secretion, and mercaptans are among the sulfur compounds causing the disagreeable odor of flatus. T-butyl mercaptan blends are often added to the odorless natural gas used for cooking and serve to warn of gas leaks. Mercaptans take part in a wide variety of chemical reactions. Their principal uses are in jet fuels, pharmaceuticals, and in gas leak or presence indicators, and the like.

In addition to the components above described, a hydrocarbon-containing material, such as diesel, gasoline, turpentine, or other product which emits an order detectible by a meter or the like and that may be carried by the gas carrier, may also be used as the marker component.

As used herein and in the appended claims, the phrase "a weld connecting a wellhead to a casing" shall include not only welds connecting a wellhead to a casing, but also to welds and the like connecting one or more components or parts comprising a pressure vessel, such as a tank, or the like.

What is claimed and desired to be secured by Letters Patent is:

1. A method of detecting flaws in a weld connecting a wellhead to a casing, the method comprising the steps of:
   (a) providing a source of pressurized gas;
   (b) providing an indicator chamber having a housing having upstream and downstream ends and means housed within said chamber housing between said housing ends for receipt of an indicator composition including a marker component impregnated onto a surface within said chamber;
   (c) securing a first conduit between said source of pressurized gas and the upstream end of said housing;
   (d) securing a second conduit between the downstream end of the chamber housing and an injection port in said wellhead;
   (e) injecting the pressurized gas from the source into said first conduit and across the means for receipt of an indicator composition within the chamber housing to form a pressurized gas indicator composition, said pressurized gas indicator composition comprising a mixture of gas from said source and at least a marking amount of the marker component;
   (f) transmitting said pressurized gas composition out of said chamber housing and into said second conduit;
   (g) injecting said pressurized gas composition into said injection port between an inner and outer weld of a terminal flange welded to a tubular pipe section or casing, while the weld is at an elevated temperature;
   (h) monitoring the source of pressurized gas composition for detecting losses in pressure; and
   (i) passing a marker gas detector probe over the weld for detecting marker component leaking through the weld.

2. The method of claim 1 wherein said marker component comprises 1,1,1,2-tetrafluoroehtane.

3. The method of claim 1 wherein said marker component comprises a halogen-containing hydrocarbon and is free of Refrigerant 12.

4. The method of claim 1 wherein the marker component includes a mercaptan.

5. The method of claim 1 wherein fluid communication is established between said pressurized gas composition and the weld while the temperature of the wellhead is at substantially 500.degrees F.

6. The method of claim 1 wherein the means for receipt of said indicator component includes a surface selectively insertable within and removable from said chamber.

7. The method of claim 1 wherein the marker component is a hydrocarbon.

8. A system for determining flaws in a weld connecting a terminal flange to a pipe, comprising:
   (a) a source of pressurized gas;
   (b) an indicator housing and a chamber therein, said housing further having upstream and downstream ends;
   (c) means within said chamber for receipt of an indicator composition comprising a marker component impregnated onto a surface within said chamber;
   (d) a first conduit between said source of pressurized gas and the upstream end of said housing for introducing said pressurized gas into said chamber to thereafter carry the marker component of the indicator composition in the pressurized gas gas out of the chamber;
   (e) a second conduit between the downstream end of the chamber housing and an injection port in said wellhead for transmitting the combined pressurized gas gas and a marking amount of the marker component therein and over the weld; and
   (f) a detector probe for detecting the presence of the marker component leaking through said weld, wherein fluid communication is established between said pressurized gas composition and the marker component and said weld while the weld is maintained at an elevated welding temperature for detecting flaws in said weld at said elevated temperature.

9. The system of claim 8 wherein said marker component comprises 1,1,1,2-tetrafluoroethane.

10. The system of claim 8 wherein said marker component is a non chlorine-containing hydrofluorocarbon.

11. The system of claim 8 wherein said marker component is free of Refrigerant 12.

12. The system of claim 8 wherein said marker component comprises a mercaptan.

13. The system of claim 8 wherein said marker component comprises a chlorine-containing component.

14. The system of claim 8 wherein the means for receipt of said indicator composition comprises a surface selectively removable from and introducible within said chamber.

15. A method of detecting flaws in a weld connecting a wellhead to a casing, the method comprising the steps of:
   (1) providing a source of pressurized gas;
   (2) providing an indicator chamber having a housing having upstream and downstream ends and means housed within said chamber housing between said housing ends for receipt of an indicator composition including a marker component impregnated onto a surface within said chamber;
   (3) securing a first conduit between said source of pressurized gas and the upstream end of said housing;
   (4) securing a second conduit between the downstream end of the chamber housing and an injection port in said wellhead;
   (5) injecting the pressured gas from the source into said first conduit and across the removable surface within the chamber housing to form a pressurized gas indicator composition, said pressurized gas indicator composition comprising a mixture of gas from said source and at least a marking amount of said marker component;
   (6) transmitting said pressurized gas composition out of said chamber housing and into said second conduit;
   (7) injecting said pressurized gas composition into said injection port between an inner and outer weld of a terminal flange welded to a tubular pipe section or casing, while the weld is at an elevated temperature; and
   (8) monitoring the source of pressurized gas composition for detecting losses in pressure.

16. A method of detecting flaws in a weld connecting a wellhead to a casing, the method comprising the steps of:
   (a) providing a source of pressurized gas;
   (b) providing an indicator chamber having a housing having upstream and downstream ends and means housed within said chamber housing between said housing ends for receipt of an indicator composition including a marker component impregnated onto a surface within said chamber;
   (c) securing a first conduit between said source of pressurized gas and the upstream end of said housing;
   (d) securing a second conduit between the downstream end of the chamber housing and an injection port in said wellhead;

(e) injecting the pressurized gas from the source into said first conduit and across the means for receipt of an indicator composition within the chamber housing to form a pressurized gas indicator composition, said pressurized gas indicator composition comprising a mixture of gas from said source and at least a marking amount of the marker component;

(f) transmitting said pressurized gas composition out of said chamber housing and into said second conduit;

(g) injecting said pressurized gas composition into said injection port between an inner and outer weld of a terminal flange welded to a tubular pipe section or casing, while the weld is at an elevated temperature; and (h) passing a marker gas detector probe over the weld for detecting marker component leaking through the weld.

17. A method of detecting flaws in a wall portion of a pressure vessel having an injection port, the method comprising the steps of:

(j) providing a source of pressurized gas;

(k) providing an indicator chamber having a housing having upstream and downstream ends and means housed within said chamber housing between said housing ends for receipt of an indicator composition including a marker component impregnated onto a surface within said chamber;

(l) securing a first conduit between said source of pressurized gas and the upstream end of said housing;

(m) securing a second conduit between the downstream end of the chamber housing and the injection port in said pressure vessel;

(n) injecting the pressurized gas from the source into said first conduit and across the means for receipt of an indicator composition within the chamber housing to form a pressurized gas indicator composition, said pressurized gas indicator composition comprising a mixture of gas from said source and at least a marking amount of the marker component;

(o) transmitting said pressurized gas composition out of said chamber housing and into said second conduit;

(p) injecting said pressurized gas composition into said injection port, while the weld is at an elevated temperature;

(q) monitoring the source of pressurized gas composition for detecting losses in pressure; and (r) passing a marker gas detector probe over the weld for detecting marker component leaking through the pressure vessel.

* * * * *